(12) United States Patent
Yang et al.

(10) Patent No.: US 11,626,207 B2
(45) Date of Patent: Apr. 11, 2023

(54) METHODS AND SYSTEMS FOR PROVIDING CUSTOMIZED SETTINGS FOR PATIENT MONITORS

(71) Applicant: KONINKLIJKE PHILIPS N.V., Eindhoven (NL)

(72) Inventors: Lin Yang, Chandler, AZ (US); Cornelis Conradus Adrianus Maria van Zon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 16/301,534

(22) PCT Filed: May 24, 2017

(86) PCT No.: PCT/EP2017/062686
§ 371 (c)(1),
(2) Date: Nov. 14, 2018

(87) PCT Pub. No.: WO2017/203002
PCT Pub. Date: Nov. 30, 2017

(65) Prior Publication Data
US 2019/0295696 A1    Sep. 26, 2019

Related U.S. Application Data

(60) Provisional application No. 62/340,712, filed on May 24, 2016.

(51) Int. Cl.
*G16H 40/63* (2018.01)
*G16H 10/60* (2018.01)
(Continued)

(52) U.S. Cl.
CPC .............. *G16H 40/63* (2018.01); *A61B 5/746* (2013.01); *G16H 10/60* (2018.01); *G16H 40/67* (2018.01); *G16H 50/20* (2018.01)

(58) Field of Classification Search
CPC ........ G16H 10/60; G16H 40/60; G16H 50/20; G06F 19/34; A61B 5/00; A61B 5/746
See application file for complete search history.

(56) References Cited

U.S. PATENT DOCUMENTS

2008/0235058 A1    9/2008  Friedman et al.
2009/0171167 A1    7/2009  Baker, Jr.
(Continued)

FOREIGN PATENT DOCUMENTS

WO    WO-2011116340 A2 *  9/2011  ......... G06F 19/3418

OTHER PUBLICATIONS

Cvach, Maria. "Monitor alarm fatigue: an integrative review." Biomedical instrumentation & technology 46.4 (2012): 268-277. (Year: 2012).*

(Continued)

*Primary Examiner* — Robert W Morgan
*Assistant Examiner* — Chance L Smith

(57) ABSTRACT

A method for providing one or more customized alarm setting recommendations for a patient includes the steps of: providing a patient monitor configured to monitor the patient, the patient monitor comprising a patient sensor and a processor configured to receive the sensor data from the patient sensor, receiving, by the patient monitor, information about a patient; analyzing, by the processor using an alarm setting recommendation classifier, the received information about the patient to generate one or more alarm setting recommendations customized to the patient; providing the one or more alarm setting recommendations to the user, and receiving input from the user accepting, rejecting, and/or modifying the alarm setting recommendations.

16 Claims, 6 Drawing Sheets

(51) Int. Cl.
  *A61B 5/00* (2006.01)
  *G16H 50/20* (2018.01)
  *G16H 40/67* (2018.01)

(56) References Cited

U.S. PATENT DOCUMENTS

| | | | | |
|---|---|---|---|---|
| 2012/0145152 | A1* | 6/2012 | Lain | G06F 19/34 128/204.23 |
| 2014/0279754 | A1 | 9/2014 | Barsoum | |
| 2015/0137968 | A1* | 5/2015 | Rusin | G08B 25/001 340/506 |
| 2015/0205931 | A1* | 7/2015 | Wang | G16H 40/63 702/19 |
| 2015/0241406 | A1 | 8/2015 | Rexzka | |
| 2015/0364022 | A1* | 12/2015 | Dyell | A61B 5/746 340/573.1 |
| 2016/0022140 | A1* | 1/2016 | Colman | A61B 5/746 340/539.12 |
| 2016/0026762 | A1* | 1/2016 | Radhakrishnan | G16H 40/67 705/3 |
| 2016/0051206 | A1* | 2/2016 | De Waele | A61B 5/0205 600/301 |
| 2016/0078750 | A1* | 3/2016 | King | A61B 5/002 340/506 |

OTHER PUBLICATIONS

Imhoff, Michael, and Silvia Kuhls. "Alarm algorithms in critical care monitoring." Anesthesia & Analgesia 102.5 (2006): 1525-1537. (Year: 2006).*

Schmid, Felix, Matthias S. Goepfert, and Daniel A. Reuter. "Patient monitoring alarms in the ICU and in the operating room." Critical care 17.2 (2013): 1-7. (Year: 2013).*

* cited by examiner

METHODS AND SYSTEMS FOR PROVIDING CUSTOMIZED SETTINGS FOR PATIENT MONITORS

CROSS-REFERENCE TO PRIOR APPLICATIONS

This application is the U.S. National Phase application under 35 U.S.C. § 371 of International Application No. PCT/EP2017/062686, filed on May 24, 2017, which claims the benefit of U.S. Provisional Application No. 62/340,712, filed May 24, 2016. These applications are hereby incorporated by reference herein, for all purposes.

TECHNICAL FIELD

The present disclosure is directed generally to methods and systems for patient monitoring, and more specifically, to methods and systems for customizing monitoring settings for individual patients.

BACKGROUND

Patient monitoring in a clinical setting is an essential component of both acute and long-term patient care. Automated or semi-automated monitoring allows multiple patients to receive care without the full-time presence of a health-care professional, thereby reducing costs and increasing health-care efficiency. One important component of patient monitoring is detecting and reporting patient deterioration. Generally, when patient deterioration is detected one or more notifications or alarms are generated that alert clinicians to provide the proper level of attention to that particular patient. Many deterioration detection algorithms set pre-defined or pre-determined criteria and thresholds. When a monitored risk indicator passes pre-defined or pre-determined criteria or thresholds, an alarm can be generated.

Various medical devices or software platforms used in a clinical setting have integrated different types of alarms, each of which can be sensitive to a particular clinical condition or the failure of one organ system, for example. Although these alarms have an important role in monitoring patients, collectively they can generate a significant number of alarms and notifications. If some of these notifications or alarms are not considered clinically significant by clinicians, they can add an additional burden to an already busy hospital and can distract clinicians from patient care.

SUMMARY

The present disclosure is directed to methods and systems for customizing monitoring settings for a patient. Applied to a patient monitoring system configured to provide customized alarm settings to a health care provider, the inventive methods and systems encourage health care providers to use customized patient monitoring settings, and as a result reduces alarm load and alarm fatigue in the clinical setting. The patient monitoring system can also utilize input from health care providers in order to learn and improve the accuracy of customized settings and recommendations.

Generally in one aspect, a patient monitoring system configured to provide one or more customized alarm setting recommendations for a patient is provided. The patient monitoring system includes: a patient sensor configured to obtain sensor data from the patient; a display configured to display one or more customized alarm setting recommendations to a user; a user interface configured to receive input from the user; and a processor configured to receive the sensor data from the patient sensor, and further configured to: (i) receive information about the patient; (ii) analyze, using an alarm setting recommendation classifier, the received information; (iii) generate, based on the analysis, one or more customized alarm setting recommendations; (iv) provide the one or more customized alarm setting recommendations to a user to the display; and (v) receive input from the user interface regarding the one or more customized alarm setting recommendations.

According to an embodiment, the one or more customized alarm setting recommendations comprises an upper limit for the obtained sensor data or a lower limit for the obtained sensor data.

According to an embodiment, the alarm setting recommendation classifier comprises a set of recommendation rules.

According to an embodiment, the information about the patient comprises one or more of demographic information about the patient, a diagnosis of the patient, a vital sign of the patient, and a prior treatment of the patient.

According to an embodiment, the patient monitoring system further includes a database configured to store the alarm setting recommendation classifier.

According to an aspect, a method for generating an alarm setting recommendation classifier is provided. The method includes the steps of: collecting information about a plurality of patients; collecting one or more alarm settings for patient monitors associated with the plurality of patients; collecting sensor data from the patient monitors; creating a database comprising the collected information about the patient and the collected one or more alarm settings; analyzing the database to create the alarm setting recommendation classifier.

According to an embodiment, the alarm setting recommendation classifier is a random forest classifier.

According to an embodiment, the method further includes the step of generating, using the alarm setting recommendation classifier and information about a second patient, one or more alarm setting recommendations for the second patient, where the generated one or more alarm setting recommendations are customized to the second patient.

According to an embodiment, the method further includes the step of communicating, to a user, the one or more alarm setting recommendations for the patient.

According to an aspect, a method for providing one or more customized alarm setting recommendations for a patient is provided. The method includes the steps of: providing a patient monitor configured to monitor the patient, the patient monitor comprising a patient sensor configured to obtain sensor data from the patient, and a processor configured to receive the sensor data from the patient sensor; receiving, by the patient monitor, information about a patient; analyzing, by the processor using an alarm setting recommendation classifier, the received information about the patient to generate one or more alarm setting recommendations for the patient monitor, wherein the generated one or more alarm setting recommendations are customized to the patient;

According to an embodiment, the method further includes the step of providing the one or more alarm setting recommendations to the user; and receiving input from the user regarding the one or more alarm setting recommendations, wherein the input comprises an acceptance of the one or more alarm setting recommendations, a rejection of the one or more alarm setting recommendations, or a modification of the one or more alarm setting recommendations.

According to an embodiment, the method further includes the step of automatically instituting, by the patient monitor, the one or more alarm setting recommendations for the patient monitor.

According to an embodiment, the method further includes the step of updating, using the input from the user regarding the one or more alarm setting recommendations, the alarm setting recommendation classifier.

As used herein for purposes of the present disclosure, the term "controller" is used generally to describe various apparatus relating to the operation of a ventilator apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, digital signal processors (DSPs), application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects discussed herein. The terms "program" or "computer program" are used herein in a generic sense to refer to any type of computer code (e.g., software or microcode) that can be employed to program one or more processors or controllers. As used herein, the term "non-transitory machine-readable medium" will be understood to encompass both volatile and non-volatile memories, but to exclude transitory signals.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, mice, keyboards, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles.

DETAILED DESCRIPTION OF EMBODIMENTS

One challenge faced by patient monitoring systems is that despite the significant and substantial variability between patients, most clinical settings and monitoring systems use either factory—or institutional-defined or default alarm settings. These predefined or default settings are often derived from large databases of population data rather than the specific individual. As such, a predefined or default alarm or notification setting is unable to sufficiently meet the deterioration detection requirement of every individual patient. As just one example, a $SpO_2$ greater than 95% is considered normal for the general population, but patients with stable COPD often have lower baseline $SpO_2$. The goal of long-term treatment of stable COPD is to maintain $SpO_2 > 90\%$, and in this case using the same $SPO_2$ threshold for all patients would either miss deterioration in the general patient population or cause too many false alarms in COPD patients.

It is traditionally recommended that monitor users such as nurses, physicians, and monitor technicians adjust alarm settings manually based on the individual patient. However, the patient to nurse ratio in ICU is often 2 to 1, and the number can be as much as to 8 to 1 in a general ward. In a remote tele-monitoring center, a health care professional may monitor more than 20 patients simultaneously. Manually changing all the possible alarm settings of every patient under the professional's care requires an excessive amount of time and therefore could stop a user from doing so. In addition, without a given protocol, monitor users may not have enough information or experience to determine the optimal alarm settings. As a result, factory—or institutional-defined or default alarm settings are most commonly used, and alarm fatigue has become a critical issue in many health care settings.

Accordingly, it would be beneficial to provide systems and methods for customizing monitoring settings for individual patients, thereby alleviating alarm fatigue and the workload of health care professionals.

The present disclosure describes various embodiments of a method and system for patient monitoring. More generally, Applicant has recognized and appreciated that it would be beneficial to provide a system to efficiently customize monitoring settings for a specific patient in order to reduce workload and alarm fatigue. Accordingly, the methods and systems described or otherwise envisioned herein provide a patient monitoring system configured to recommend customized alarm settings to a health care provider, and to utilize feedback in order to improve future recommendations. According to an embodiment, the system includes a tracking component that tracks is a user manually changes alarm settings, a data collection component to collect patient data such as vital signs and diagnosis, a data mining component to derive new alarm setting rules, and a feedback component to test and update the new alarm setting rules.

Figure 1:
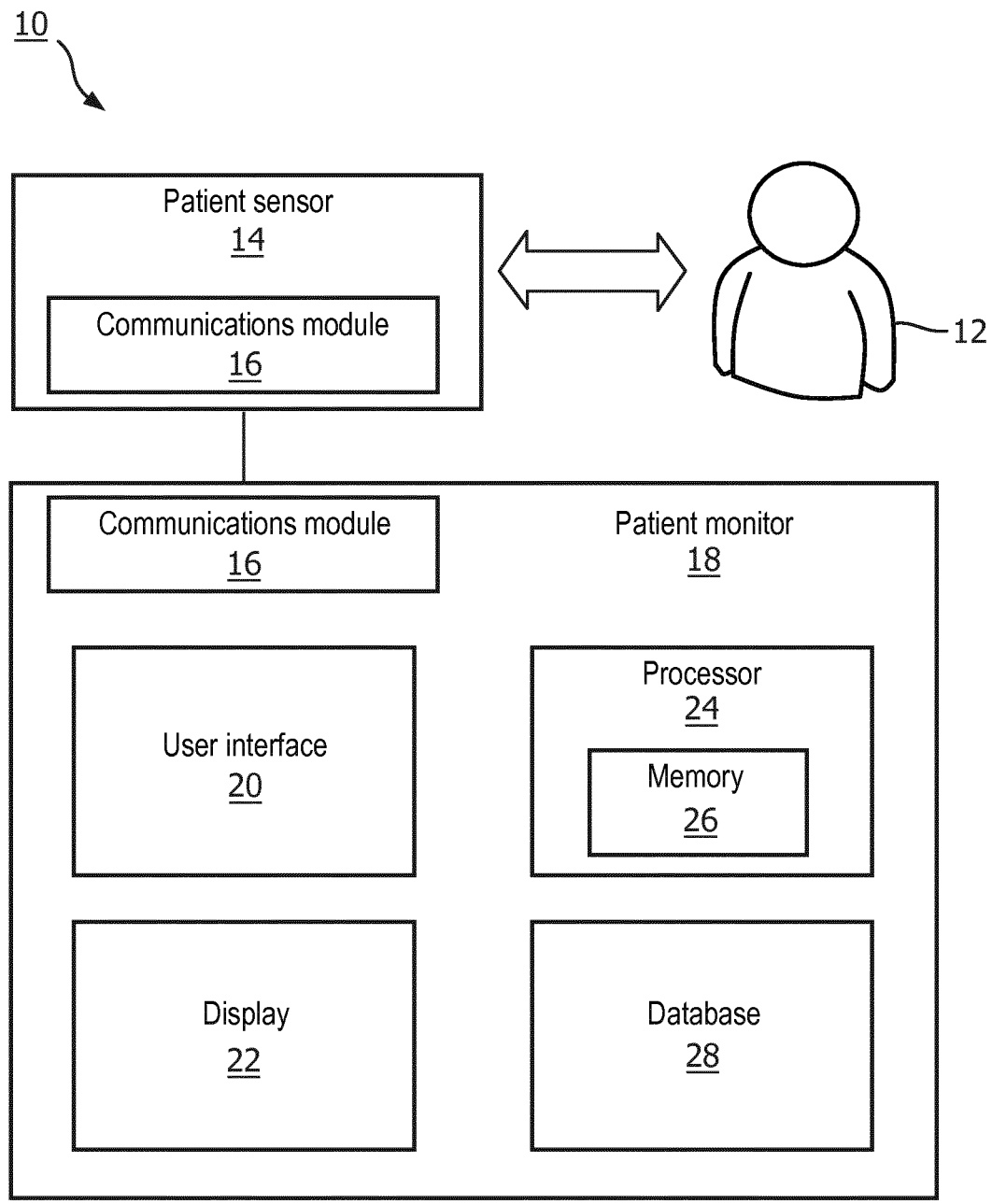
FIG. 1 is a schematic representation of a patient monitor, in accordance with an embodiment.

Referring to FIG. 1, in one embodiment, is a patient monitoring system 10. The patient monitoring system can be any system described or otherwise envisioned herein. According to an embodiment, patient monitoring system 10 comprises one or more patient sensors 14 which interface either directly or remotely with the patient 12. The patient sensor can be a sensor or other suitable medical device such as a therapy device. For example, patient sensor 14 can be any heart rate sensor, breathing sensor, blood pressure sensor, blood oxygen saturation sensor, neurological sensor, blood glucose sensor, temperature sensor, or any other type of sensor. Patient sensor 14 can also be a therapy device such as a respirator or any other type of therapy device.

According to an embodiment, the patient sensor communicates with a patient monitor 18 via a wired and/or wireless communications link. Accordingly, both the patient sensor and the patient monitor 18 can comprise a communications module 16 to facilitate the wired and/or wireless communications between the patient sensor and the patient monitor. Wireless communications may be conducted over one or more wireless networks, including but not limited to Wi-Fi, Bluetooth®, 3G, 4G, LTE, ZigBee®, and other networks.

Patient monitor 18 may also comprise a user interface 20, which can be configured to receive input from a health care provider regarding one or more settings for the monitoring system. The user interface 20 may include one or more selectable inputs such as buttons, knobs, slide bars, joysticks, or others to receive input to change the information shown on the display or to change information received by the system from the user. The monitor may also comprise a display 22 configured to display information received from the patient sensor, to enable input via the user interface, and/or to display one or more settings for the patient monitoring system. The display 22 may be used to display various types of information or facilitate interaction between the user and system (e.g., GUI). In some embodiments, the display 22 can be cathode ray tube-based, LED-based, LCD-based, projection-based, head-mount-based, or e-paper type display. According to one embodiment the user interface 20 and display 22 are separate components, but display 22 may also be utilized as the user interface in other embodiments. For example, the display 22 may be a touch screen display that allows the user to directly interact with the system through physical contact and/or gestures. In general, the display 22 may show physiological data and/or other data received from patient sensor 14, among other data.

According to an embodiment, the display 22 may be configured to display patient data such as a breathing waveform, oxygen saturation, blood pressure, and/or a pulse rate. The display 22 may also be configured to display user interface options, such as a configuration screen for adjusting one or more patient monitoring parameters or settings, including but not limited to a minimum and/or maximum value for a patient sensor in order to trigger an alarm, alarm settings such as volume and notification method, and others. For example, the display 22 may display upper and/or lower alarm limits—and the ability to change these limits—for the breathing waveform, oxygen saturation, blood pressure, and/or pulse rate among other possible sensor data. If an upper or lower alarm limit is exceeded the system may produce an alarm, which may be an audible, visible, and/or haptic alarm, among other possible alarms. The alarm may be duplicated on or limited to central monitoring stations, sent to care provider smart phones or pagers, etc. The display 22 may also include one or more inputs for alarm management, including a snooze input, inactivation input, and other inputs.

According to an embodiment, patient monitor 18 further comprises a processor 24 which receives the information generated by the one or more patient sensors 14. Processor 24 may take any suitable form, and may be formed of one or multiple modules. For example, processor 24 may be or include a microcontroller, plural microcontrollers, circuitry, a single processor, or plural processors. Processor 24 may also include a memory 26, which can take any suitable form including a non-volatile memory (e.g., flash, optical, or magnetic storage) and/or volatile memory (e.g SRAM or DRAM). It will be apparent that in some embodiments the memory 26 or portions thereof my not be physically on the same chip as the processor and, instead, may be in communication with the computer via one or more buses or interfaces. The non-volatile memory may include read only memory (ROM), a hard disk drive (HDD) or a solid state drive (SSD). The memory can store, among other things, an operating system. The RAM is used by the processor for the temporary storage of data. The operating system may contain code which, when executed by processor 24, controls operation of each of the hardware and/or software components of the patient monitoring system 10. As set forth in greater detail below, the processor may comprise a recommendation classifier which can be utilized to provide one or more alarm setting recommendations customized to the monitored patient.

According to an embodiment, patient monitor 18 further comprises a database 28 which can include patient data, historical monitoring data, patient monitoring systems settings, and other information as described or otherwise envisioned herein. For example, the patient data may include demographics, diagnosis, and baseline vital signs which can be utilized for alarm setting recommendations as set forth herein. Alternatively, the system can retrieve this information from an electronic medical record database. As set forth in greater detail below, the database may comprise a recommendation classifier which can be utilized to provide one or more alarm setting recommendations customized to the monitored patient. In some embodiments, the database 28 may be stored in the memory 26.

Although the components of the patient monitor 18 are shown as a single unit, one or more of these components may be located remotely from the patient monitor. For example, according to one embodiment the database 28 is located remotely from the patient monitor. Many other combinations are possible.

Figure 2:
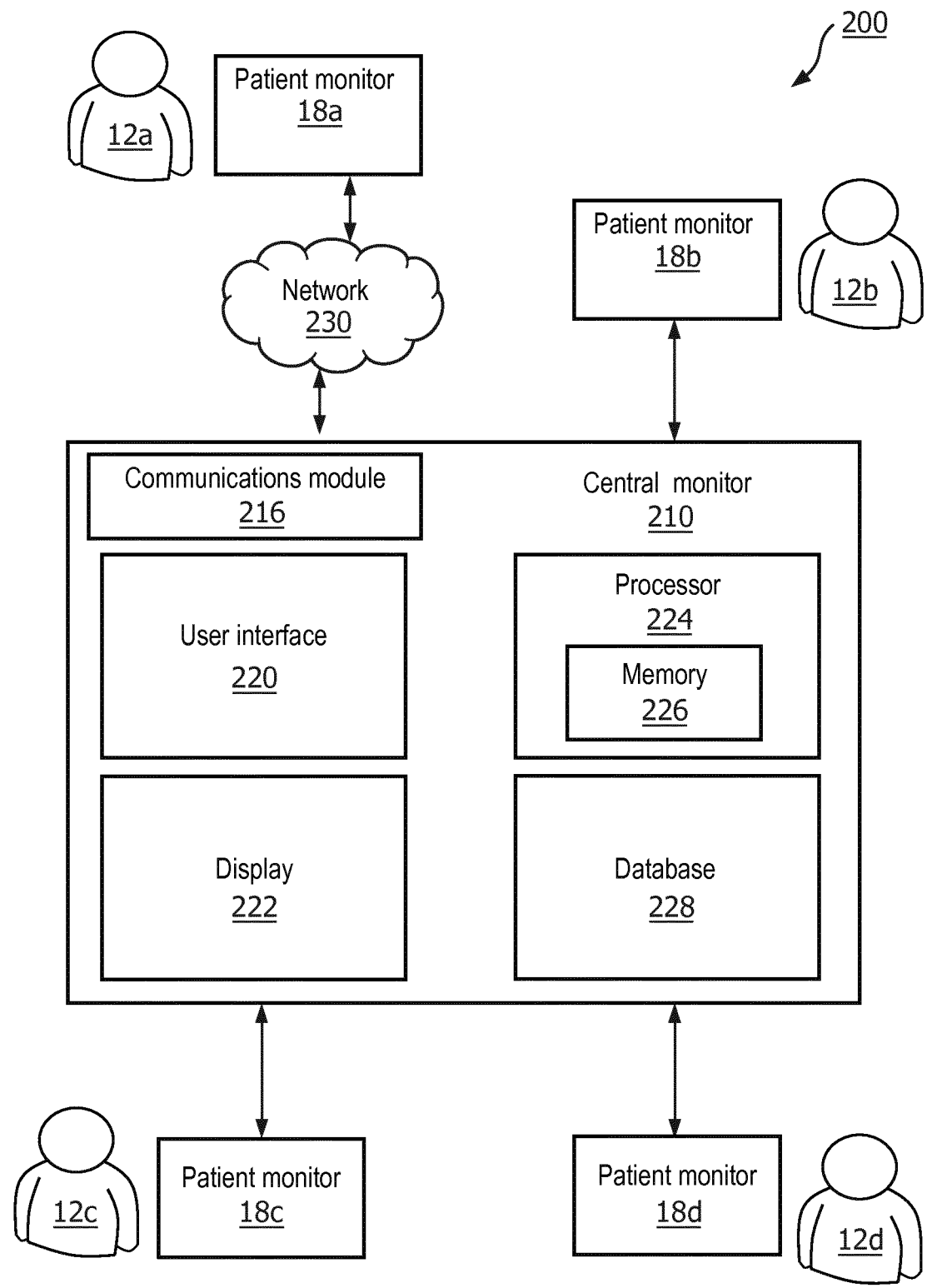
FIG. 2 is a schematic representation of a patient monitoring system, in accordance with an embodiment.

Referring to FIG. 2, in one embodiment, is a central monitoring system 200 comprising a central monitor 210 and a plurality of patient monitors 18a, 18b, 18c, and 18d. Each of the plurality of patient monitors 18 monitor one or more patients 12 as described above with reference to FIG. 1, and each comprise one or more patient sensors 14 which interface either directly or remotely with the patient 12. According to an embodiment, the central monitor 210 comprises a wired and/or wireless communications module 216 to communicate with each of the plurality of patient monitors 18a, 18b, 18c, and 18d. The wired and/or wireless communications may comprise a network 230, including but not limited to Ethernet, Wi-Fi, Bluetooth®, 3G, 4G, LTE, ZigBee®, and other networks.

The central monitoring system 200 may comprise a user interface 220 configured to receive input from a health care provider regarding one or more settings for the system and/or one or more settings for one or more of the patient monitors 18a, 18b, 18c, and 18d. The central monitoring system 200 may also comprise a display 222 configured to display patient data and provide alarm notifications, a processor 224 which receives the information generated by the plurality of patient monitors, a memory 226 which may include volatile and/or non-volatile memory disposed on chip with the processor 224 and/or physically separate from but in communication with the processor 224, and a database 228 which can include patient data, historical monitoring data, patient monitoring systems settings, and other information as described or otherwise envisioned herein. In some embodiments, the database 228 may be stored within the memory 226.

Figure 3:
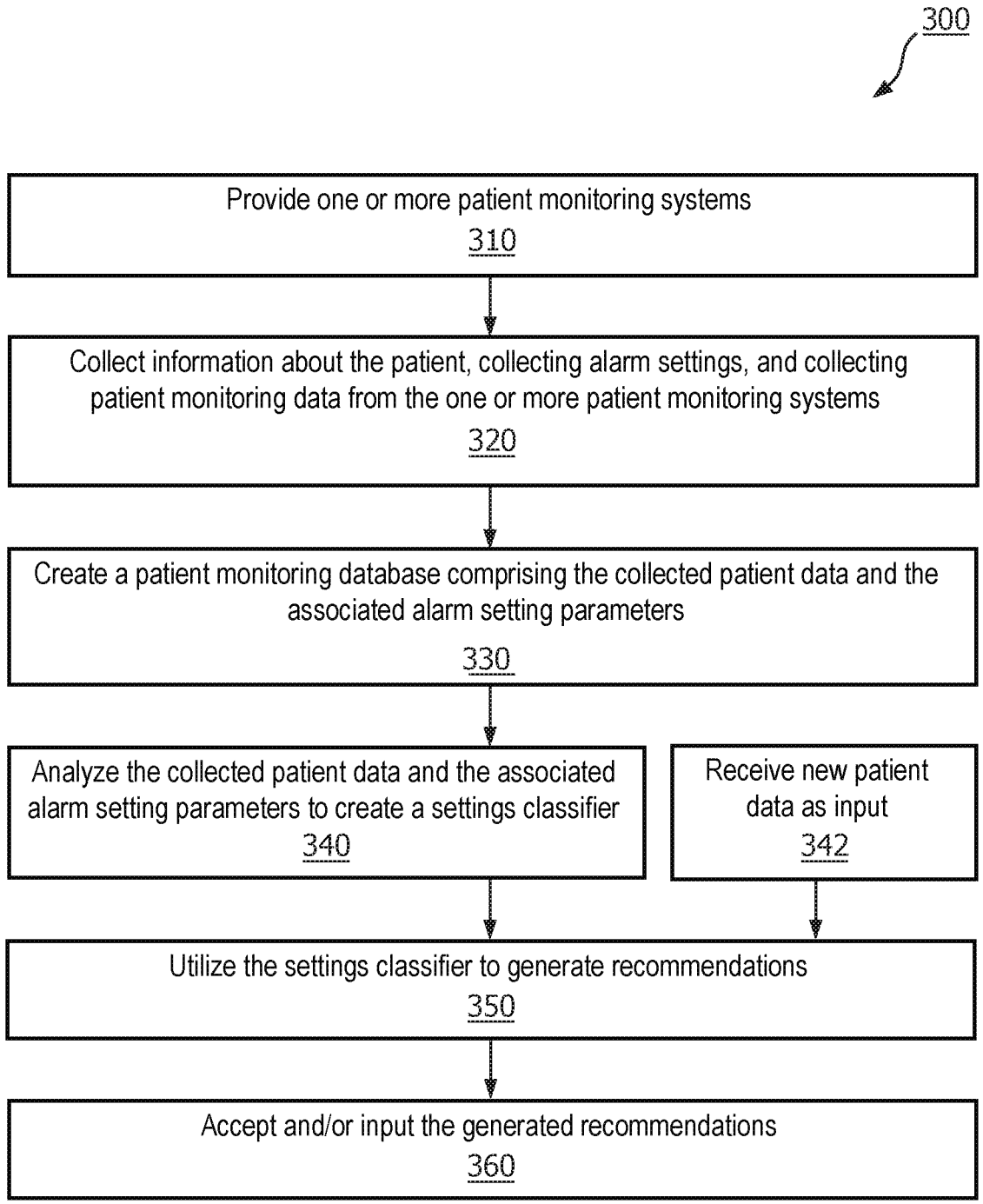
FIG. 3 is a flowchart depicting a method for creating a recommendation classifier, in accordance with an embodiment.

Referring to FIG. 3, in one embodiment, is a method 300 for generating customized monitoring settings for individual patients. According to an embodiment, the method comprises the creation of a settings recommendation database and the derivation of customized alarm settings from the generated database. The data collection for the settings recommendation database can be conducted, for example, in a trial setting where patient monitor users such as nurses, physicians, and monitor technicians manually change alarm settings for individual patients based on their clinical knowledge. The data collection for the settings recommendation database can also or alternatively be conducted, for example, in health care facilities where manual changes of alarm settings by patient monitor users are common.

At step 310 of the method, one or more patient monitoring systems are provided. The method may utilize any embodiment of the patient monitoring system 10 and/or central monitoring system 200 described or otherwise envisioned herein, in addition to other patient monitoring systems. For example, the patient monitoring system may comprise one or more patient sensors 14 which interface either directly or remotely with the patient 12, a wired and/or wireless communications module 16, a user interface 20 configured to receive input from a health care provider regarding one or more settings for the monitoring system, a display 22 configured to display patient data and provide alarm notifications, a processor 24 which receives the information generated by the one or more patient sensors, and a database 28 which can include patient data, historical monitoring data, patient monitoring systems settings, and other information as described or otherwise envisioned herein.

At step 320 of the method, information is collected by the system. For example, the system can collect information about the patient, collect alarm settings, and/or collect patient monitoring data from the one or more patient monitoring systems. For example, the one or more patient monitoring systems may comprise a tracking component which is integrated into a patient monitor 18 and/or a central monitoring system 200. The tracking component may be, for example, a software plugin, program, application, or other component. According to an embodiment, the tracking component is configured to detect when a user changes an alarm setting. The tracking component then triggers a data collection component to collect patient data from the monitor itself or from other systems, such as a monitor data server and/or a central monitoring system 200. Whenever the user manually adjusts an alarm setting, the data collection component collects patient data such as key words excerpted from a diagnosis, a baseline vital sign, an admission vital sign, demographics, and/or other data.

At step 330, the collected patient data and the associated alarm setting parameters are aggregated into a database. The database may be a database 28 of a patient monitor 18, a database 228 of the central monitoring system 200, a local database, and/or a remote database. For example, according to one embodiment, the collected patient data and the associated alarm setting parameters from multiple locations are aggregated into a single, remote database.

At step 340, according to an embodiment, the collected patient data and the associated alarm setting parameters in the database are analyzed and utilized to train a classifier that can organize and categorize the information for use in making recommendations. According to an embodiment, the classifier is a random forest classifier, which operates by constructing a multitude of decision trees during training. According to an embodiment, patient data such as demographics, diagnosis, and baseline vital signs is used as input to the random forest and the associated manually-selected new alarm setting parameters are used as standards to train the classifier. The resultant classifier can be, therefore, a series of alarm setting recommendation rules that can receive a new patient's data as input and output one or more recommendations for alarm settings customized to the patient. The one or more recommendations for alarm settings will be determined, therefore, by the analysis and classification of the collected patient data and the associated alarm setting parameters in the database. According to an embodiment, the system utilizes one or more other data mining methods, such as regression, decision trees, and/or SVM instead of a random forest classifier method in order to derive alarm setting recommendation rules.

Accordingly, at step 350 of the method, the generated classifier is utilized to generate one or more recommendations for alarm settings customized to a new patient. The new patient data is provided to the system at step 342, the classifier is utilized at step 350, and one or more recommendations for alarm settings customized to the new patient are provided to the health care provider.

At step 360 of the method, according to an embodiment, the one or more alarm setting recommendations for the patient are communicated to a user such as a health care provider, and the user accepts and/or inputs the recommendations to a patient monitor 18 and/or central monitoring system 200. For example, the patient monitor may present one or more generated recommendations, such as a suite of recommendations, to the health care provider who can then accept the suite of recommendations or can modify one or more of the generated recommendations. As an example, the display can present the health care professional with a suite of recommendations for alarm settings and can additionally present a prompt for "YES," "NO," and "ADJUST SETTINGS."

Figure 4:
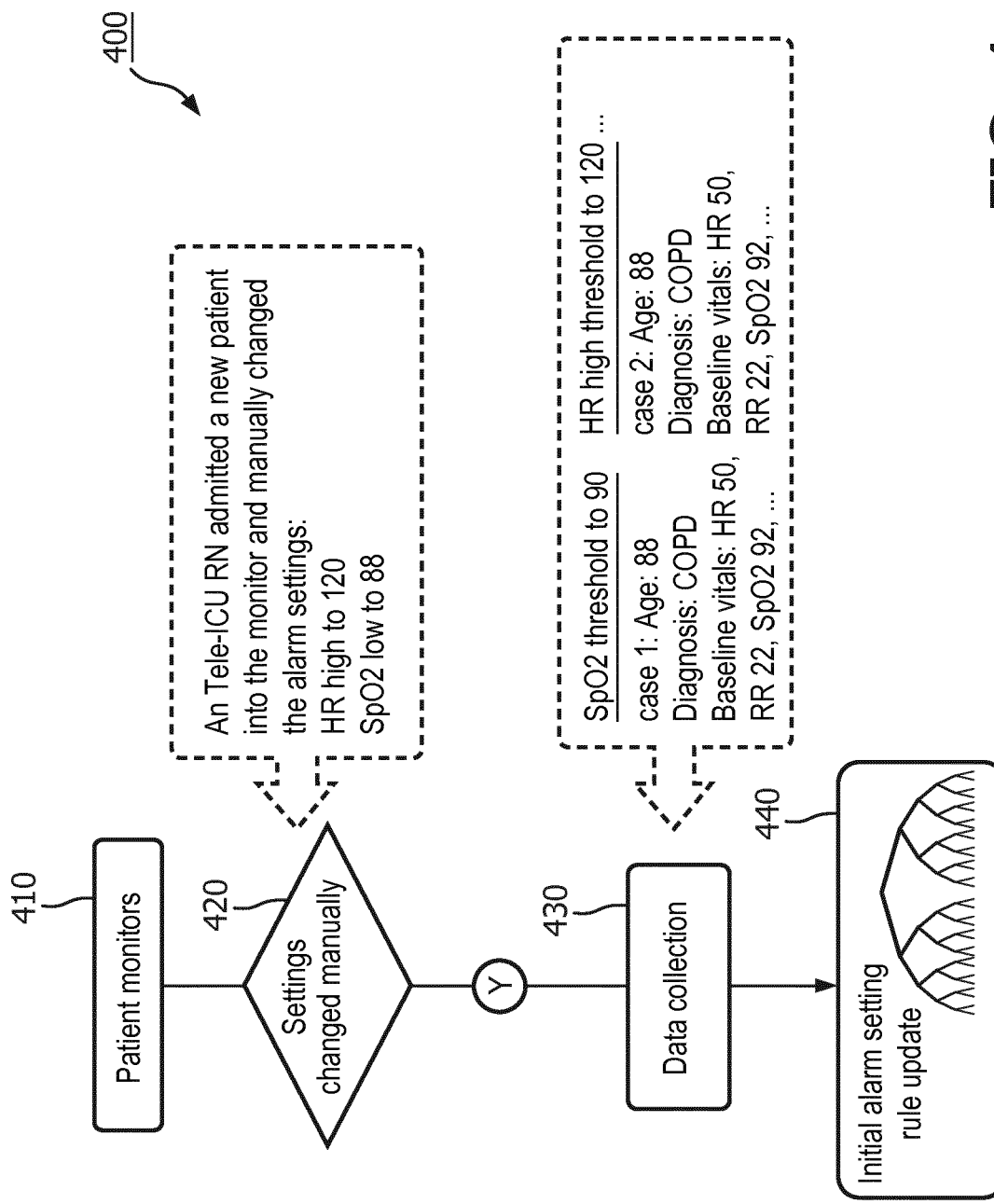
FIG. 4 is a flowchart depicting a method for creating a recommendation classifier, in accordance with an embodiment.

Referring to FIG. 4, in one embodiment, is a flowchart depicting a method 400 for generating customized monitoring settings for individual patients. According to an embodiment, at step 410 of the method, one or more patient monitoring systems are set up to monitor a patient 12. The method may utilize any embodiment of the patient monitoring system 10 and/or central monitoring system 200 described or otherwise envisioned herein, in addition to other patient monitoring systems. For example, the patient monitoring system may comprise one or more patient sensors 14 which interface either directly or remotely with the patient 12, a wired and/or wireless communications module 16, a user interface 20 configured to receive input from a health care provider regarding one or more settings for the monitoring system, a display 22 configured to display patient data and provide alarm notifications, a processor 24 which receives the information generated by the one or more patient sensors, and a database 28 which can include patient data, historical monitoring data, patient monitoring systems settings, and other information as described or otherwise envisioned herein.

At step 420 of the method, according to an embodiment, a remote health care professional such as a tele-ICU nurse—defined as a nurse monitoring one or more ICUs over distance using telecommunications technology—manually adjusts or sets an alarm setting. For example, the Tele-ICU RN registers a new patient into the central monitoring system and manually changes two alarm thresholds: the heart rate upper threshold to 120 and the $SpO_2$ lower threshold to 88%. These settings are based on the patient's demographics such as age, sex, etc., and/or on the patient's diagnosis, condition, and/or medical history.

At step 430 of the method, the patient monitoring system is triggered to collect data about the patient's care. For example, the system may collect information about the patient's care prior to the ICU admission, such as the patient's admission and general ward care. This information may be collected, for example, from electronic medical records, a data server, and/or a variety of other locations. This information is provided to a database and can be analyzed contemporaneously or at a later date. For example, the patient's data (e.g., age, main diagnosis or chronic condition, baseline vital signs, etc.) together with the new manually-determined alarm setting parameters would be put into the database as a data point. Because both the heart rate and $SpO_2$ thresholds were changed in this example, this alarm setting change action would add two new data points to the database. Similar data collection can be conducted to aggregate pairs of new alarm setting parameters and the associated patient data every time monitors' alarm settings are manually changed.

At step 440 of the method, the information collected in the database can be utilized to create or update the recommendations classifier. The recommendations classifier can be updated or revised periodically or continuously as new information is received and analyzed. For example, the appropriate machine-learning algorithm may be rerun on the updated database to train the classifier again on a periodic basis or after a threshold number of new records has been added to the database as part of the training set.

While various embodiments have been described as training a single classifier, it will be understood that in some embodiments, multiple machine-learning models may be trained using the database (or appropriate subsets thereof) for selecting recommended alarm settings. For example, different models may be associated with different individual settings (e.g., linear regression models for SpO2 threshold, HR high threshold, etc.), discrete values thereof (e.g., logistic regression models for "Alarm Type=Loud", "Alarm Type=Silent, Textual," etc.), or groups of setting values (logistic regression models for "SpO2 threshold=88, HR high threshold="88," "SpO2 threshold=90, HR high threshold="120," etc.). Accordingly, application of the classifier may in some embodiments may include application of multiple trained models (classifiers or otherwise).

Figure 5:
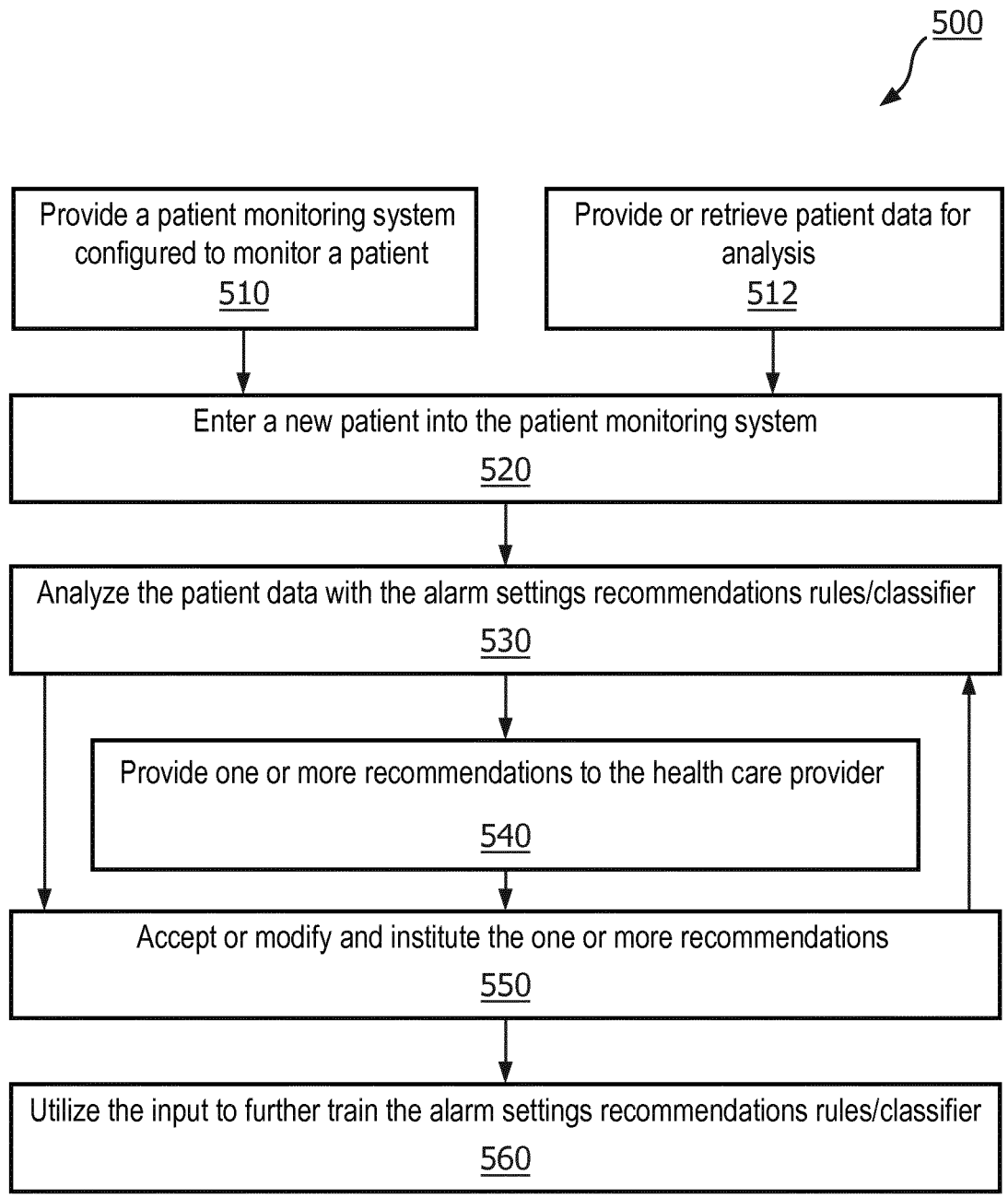
FIG. 5 is a flowchart depicting a method for creating alarm setting recommendations, in accordance with an embodiment.

Referring to FIG. 5, in one embodiment, is a flowchart depicting a method 500 for using patient monitoring settings customized for individual patients. According to an embodiment, the method comprises leveraging the generated settings recommendation classifier to provide recommendations to the health care provider based on input. Accordingly, the alarm setting recommendation rules are integrated or provided to the patient monitor 18, and every time a user registers a new patient into a monitor, the system triggers the collection of the patient's data from EMR, eCareManager, or the monitor data server, and resulting recommendations are provided to the user. Input from the users can be utilized to automatically update the recommendation method.

At step 510 of the method, a patient monitoring system configured to monitor a patient is provided. The method may utilize any embodiment of the patient monitoring system 10 described or otherwise envisioned herein, in addition to other patient monitoring systems. For example, the patient monitoring system may comprise one or more patient sensors 14 which interface either directly or remotely with the patient 12, a wired and/or wireless communications module 16, a user interface 20 configured to receive input from a health care provider regarding one or more settings for the monitoring system, a display 22 configured to display patient data and provide alarm notifications, a processor 24 which receives the information generated by the one or more patient sensors, and a database 28 which can include patient data, historical monitoring data, patient monitoring systems settings, and other information as described or otherwise envisioned herein.

According to an embodiment, the patient monitor 18 and/or central monitoring system 200 comprises the recommendation classifier as a software or hardware add-on, or the recommendation classifier is an integral part of the device or system. According to another embodiment, the patient monitor 18 and/or central monitoring system 200 access the recommendation classifier remotely to create alarm setting recommendations. Accordingly, the recommendation classifier may be a SaaS or other cloud- or remotely-based service or system that the health care facility or provider may purchase, subscribe to, or otherwise access.

At step 520 of the method, the health care provider enters a new patient into the monitoring system. The entry can comprise information about the patient, such as demographics, vitals, prior care, medical condition, diagnosis, and other information, and/or the system can retrieve that information remotely, as shown in step 512 of the method. Accordingly, the system may send queries to a remote server for data about the patient. The remote server may comprise electronic medical records, a management system such as eCareManager, or other information.

At step 530 of the method, the patient monitoring system applies the recommendation classifier to the information about the patient and generates one or more alarm setting recommendations. According to an embodiment, the alarm setting recommendations may be an upper alarm limit, a lower alarm limit, a combination of upper and lower alarm limit, no alarm setting or limit, or a wide variety of other possible alarm settings and/or limits.

At step 540 of the method, the generated one or more alarm setting recommendations are provided to the health care provider, either locally, remotely, or both. For example, the alarm setting recommendations can be automatically derived by the system and displayed on the monitor as one or more options to the user.

At step 550 of the method, the user can accept or modify the one or more recommendations. For example, the user can accept all the recommendations with a single click. Alternatively, the user may have the option to "MODIFY" in which the user can edit a particular setting and accept the rest of the recommended settings. For example, the patient monitor may present one or more generated recommendations, such as a suite of recommendations, to the health care provider who can then accept the suite of recommendations or can modify one or more of the generated recommendations. As an example, the display can present the health care professional with a suite of recommendations for alarm settings and can additionally present a prompt for "YES," "NO," and "ADJUST SETTINGS."

Alternatively, at step 550 of the method, the system receives the one or more alarm setting recommendations generated in step 530, and automatically institutes the recommendations in whole or in part. For example, the system may be designed, configured, or programmed to automatically accept generated alarm setting recommendations. The system may also be designed, configured, or programmed to automatically accept generated alarm setting recommendations within a range of possible alarm settings. A system set up to automatically accept and institute alarm setting recommendations would help further alleviate alarm fatigue and further lighten the workload of health care professionals.

At step 560 of the method, the user's input—such as modification of the provided settings—can be collected and fed back to the system. The random forest classifier will be trained and updated using the new users' data and as a result the recommendation classifier and/or alarm setting recommendation rules can be updated. At this step, the method can be used in any healthcare facilities.

Figure 6:
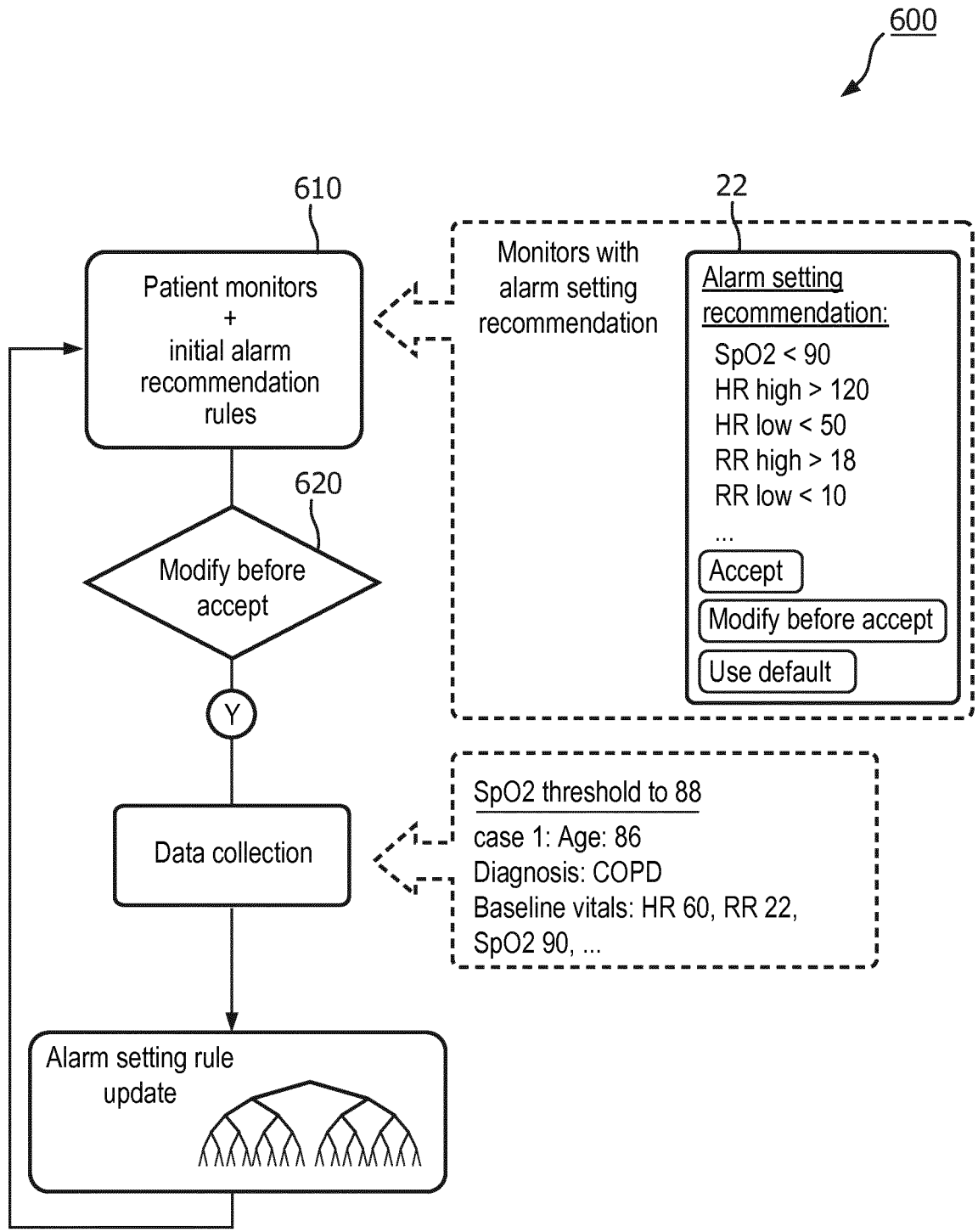
FIG. 6 is a flowchart depicting a method for creating alarm setting recommendations, in accordance with an embodiment.

Referring to FIG. 6, in one embodiment, is a flowchart depicting a method 600 for providing customized alarm recommendation settings to a health care provider. According to an embodiment, at step 610 of the method, a health care provider registers a new patient into a patient monitor or monitoring system. The health care provider provides— or the system automatically retrieves—data about the patient, such as demographics, vitals, prior care, medical condition, diagnosis, and other information. The recommendation classifier then analyze the patient's data and creates one or more alarm setting recommendations which are then provided to the health care provider. For example, the one or more alarm setting recommendations may be provided on display 22 as shown in in FIG. 6. A user interface can pop up with recommendation of one or more alarm settings.

At step 620, the health care provider—which in this example might be a remote monitoring professional—determines whether to accept, decline, and/or modify each of the recommendations. For example, the provider may be asked if he wants to "Accept" or "Decline" the recommendation. If he declines the recommendation, he has the option to use factory/institution default or to manually edit an alarm setting before accepting. If he chooses to manually set the alarm settings, the data will be collected and provided to the system to update the recommendation classifier.

Although one or more of the embodiments described above is based on remote patient monitoring systems (such as TeleICU or TeleAcute), the recommendation classifier can be also integrated into an electronic medical records (EMR) system. According to an embodiment, whenever an order is placed to put a patient on monitors, recommendations of alarm settings can be displayed in the EMR system. Users can choose to type the recommended alarm setting parameters into monitors, or can accept displayed alarm setting recommendations.

Additionally, although one or more of the embodiments described above is based on providing alarm setting recommendations when a patient is newly-entered into a system, the recommendation of alarm settings can be provided during monitoring. For example, a health care provider can choose how often they want to re-calculate the alarm setting recommendations. When a certain event happens, for example if a certain procedure is performed, the system can also recommend changing the alarm settings. Accordingly, as shown in FIG. 6 and in the method depicted in FIG. 5, for example, the method can go from step 550 back to 530 to analyze new patient data—alone or in conjunction with the previous patient data—in order to generate updated alarm setting recommendations.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A patient monitor configured to provide one or more customized alarm setting recommendations for a patient, the patient monitor comprising:
    a patient blood oxygen saturation sensor configured to obtain blood oxygen saturation sensor data from the patient;
    a display configured to display one or more customized alarm setting recommendations to a user;
    a user interface configured to receive input from the user; and
    a processor configured to receive the blood oxygen saturation sensor data from the patient blood oxygen saturation sensor and use a trained alarm setting recommendation classifier that is a machine-learning model, wherein the trained alarm setting recommendation classifier is trained using a database comprising (i) information including a vital sign about a plurality of patients, (ii) one or more alarm settings for a plurality of patient monitors associated with the plurality of patients, (iii) blood oxygen saturation sensor data from the plurality of patient monitors, and (iv) data collected from one or more user inputs, the data corresponding to one or more adjusted alarm settings;
    wherein the processor is further configured to: (i) receive information about the patient; (ii) analyze, using the trained alarm setting recommendation classifier, the received information; (iii) generate, based on said analysis, one or more customized alarm setting recommendations, wherein the generated one or more alarm setting recommendations are customized to the patient, the one or more customized alarm setting recommendations being based on a determination that the patient's blood oxygen saturation is above or below a threshold; (iv) provide the one or more customized alarm setting recommendations to a user to the display; and (v) receive input from the user interface modifying one or more customized alarm setting recommendations before an alarm is set to prevent alarm fatigue, wherein the received input modifies an upper alarm limit, a lower alarm limit, or a combination of upper and lower alarm limits for the one or more customized alarm setting recommendations.

2. The patient monitor of claim 1, wherein the one or more customized alarm setting recommendations comprises an upper limit for the obtained blood oxygen saturation sensor data or a lower limit for the obtained blood oxygen saturation sensor data.

3. The patient monitor of claim 1, wherein the alarm setting recommendation classifier machine learning model comprises a set of recommendation rules.

4. The patient monitor of claim 1, wherein the information about the patient comprises one or more of demographic information about the patient, a diagnosis of the patient, and a prior treatment of the patient.

5. The patient monitor of claim 1, further comprising a database, the database configured to store the alarm setting recommendation classifier.

6. A method for generating an alarm setting recommendation classifier, the method comprising the steps of:
    collecting, via a processor, information about a plurality of patients, wherein the information comprises a vital sign of the plurality of patients;
    collecting, via the processor, one or more alarm settings for a plurality of patient monitors associated with the plurality of patients, each configured to monitor blood oxygen saturation sensor data collected from a patient blood oxygen saturation sensor;
    collecting, via the processor, data from one or more user inputs, where the one or more user inputs corresponds to one or more adjusted alarm settings, wherein the one or more user inputs modify an upper alarm limit, a lower alarm limit, or a combination of upper and lower alarm limits from one or more default alarm settings to provide the one or more adjusted alarm settings;
    collecting, via the processor, blood oxygen saturation sensor data from the patient monitors;
    creating a database comprising the collected information about the plurality of patients, and the collected one or more alarm settings, the collected blood oxygen saturation data, and the collected data from the one or more user inputs;
    training the alarm setting recommendation classifier using the database; and
    creating an alarm setting recommendation using the trained alarm setting recommendation classifier such that the created alarm setting recommendation is modified prior to being set to prevent alarm fatigue;
    wherein the one or more customized alarm setting recommendations are based on a determination that the patient's blood oxygen saturation is above or below a threshold.

7. The method of claim 6, wherein the alarm setting recommendation classifier is a random forest classifier.

8. The method of claim 6, wherein the information about the patient comprises one or more of demographic information about the patient, a diagnosis of the patient, and a prior treatment of the patient.

9. The method of claim 6, further comprising the step of generating, using the alarm setting recommendation classifier and information about a patient, one or more alarm setting recommendations for the patient, wherein the generated one or more alarm setting recommendations are customized to the patient.

10. The method of claim 9, further comprising the step of communicating, to a user, the one or more alarm setting recommendations for the patient.

11. A method for providing one or more customized alarm setting recommendations for a patient using a trained alarm setting recommendation classifier that is a machine-learning model, wherein the trained alarm setting recommendation classifier is trained using a database comprising (i) information including a vital sign about a plurality of patients, (ii) one or more alarm settings for a plurality of patient monitors associated with the plurality of patients, (iii) blood oxygen saturation sensor data from the plurality of patient monitors, and (iv) data collected from one or more user inputs, the data corresponding to one or more adjusted alarm settings, the method comprising the steps of:
 providing a patient monitor configured to monitor the patient, the patient monitor comprising a patient blood oxygen saturation sensor configured to obtain blood oxygen saturation sensor data from the patient a display configured to display one or more customized alarm setting recommendations to a user, a user interface configured to receive input from the user, and a processor configured to receive the blood oxygen saturation sensor data from the patient sensor;
 receiving, by the patient monitor, information about the patient, wherein the information comprises a vital sign of the patient;
 analyzing, by the processor using the trained alarm setting recommendation classifier, the received information about the patient to generate one or more alarm setting recommendations for the patient monitor, wherein the generated one or more alarm setting recommendations are customized to the patient and the one or more customized alarm setting recommendations being based on a determination that the patient's blood oxygen saturation is above or below a threshold;
 providing the one or more customized alarm setting recommendations to a user to the display; and
 receiving input from the user interface modifying the one or more customized alarm setting recommendations before the alarm is set to prevent alarm fatigue, wherein the received input modifies an upper alarm limit, a lower alarm limit, or a combination of upper and lower alarm limits for the one or more customized alarm setting recommendations.

12. The method of claim 11, wherein the input comprises an acceptance of the one or more alarm setting recommendations, a rejection of the one or more alarm setting recommendations, or a modification of the one or more alarm setting recommendations.

13. The method of claim 12, further comprising the step of updating, using the input from the user regarding the one or more alarm setting recommendations, the alarm setting recommendation classifier.

14. The method of claim 11, further comprising the step of automatically instituting, by the patient monitor, the one or more alarm setting recommendations for the patient monitor.

15. The method of claim 11, wherein the information about the patient comprises one or more of demographic information about the patient, a diagnosis of the patient, a history of the patient, a lab or test result, and a prior treatment of the patient.

16. The method of claim 11, wherein the alarm setting recommendation classifier comprises more than one trained model, at least a first alarm setting recommendation for at least the one new patient is generated using a first trained model of the alarm setting recommendation classifier, and at least a second alarm setting recommendation for at least the one new patient is generated using a second trained model of the alarm setting recommendation classifier.

* * * * *